United States Patent [19]

Trott

[11] 4,228,802
[45] Oct. 21, 1980

[54] SELF-INFLATING AND SELF-CLEANING CATHETER ASSEMBLY

[75] Inventor: William A. Trott, Winnipeg, Canada

[73] Assignee: Medical Products Institute Incorporated, Winnipeg, Canada

[21] Appl. No.: 913,516

[22] Filed: Jun. 7, 1978

[30] Foreign Application Priority Data

Jun. 15, 1977 [GB] United Kingdom ............... 24960/77

[51] Int. Cl.³ ............................................. A61M 25/00
[52] U.S. Cl. ............................. 128/349 R; 128/350 R
[58] Field of Search ............... 128/348, 349 R, 349 B, 128/350, 350 R, 243, 208; 27/24 A

[56] References Cited

U.S. PATENT DOCUMENTS 3,397,699  8/1968  Kohl ................................. 128/349 R

FOREIGN PATENT DOCUMENTS 459391  9/1913  France ................................. 128/349 R
955490  4/1964  United Kingdom ................ 128/349 R Primary Examiner—Harry N. Haroian
Attorney, Agent, or Firm—Stanley G. Ade

[57] ABSTRACT

An outer envelope and an inner drainage tube are formed from an elastomeric material with molded in reinforcing and guiding elements. The inner tube engages within the outer tube to form a flexible catheter having a smooth outer surface and a pair of interior lumens. The inner cylindrical lumen through the inner drainage tube serves as a drainage channel and the second lumen, formed by the annular cross sectional space between the tubes, provides a passage for the introduction of irrigating fluid or the like. A mechanical expanding device is provided near the distal end and a manually operated actuator near the proximal or external end. A detachable auger assembly can be introduced into the first lumen and can be rotated from the external end of the catheter to draw down clots or debris from the bladder which might obstruct the passage.

18 Claims, 31 Drawing Figures

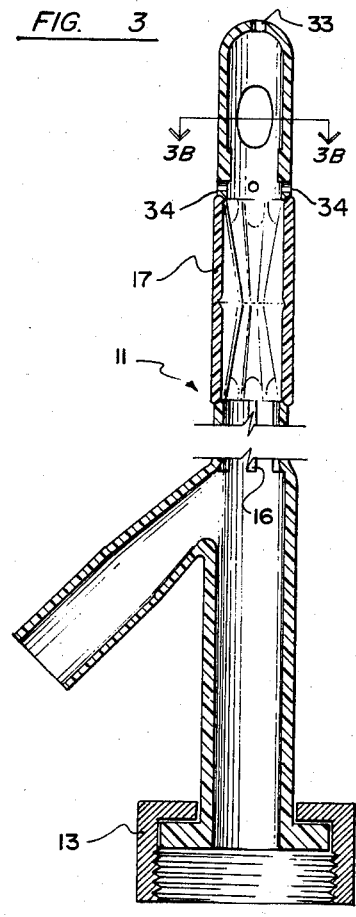
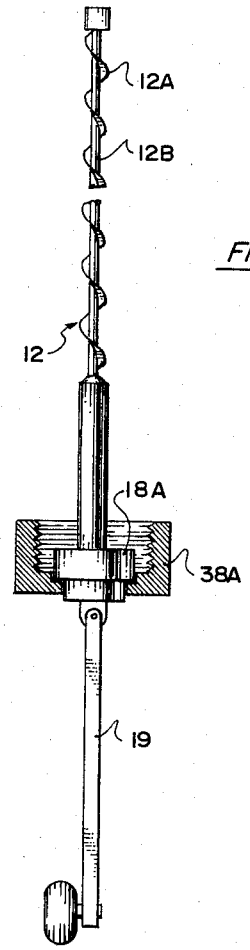
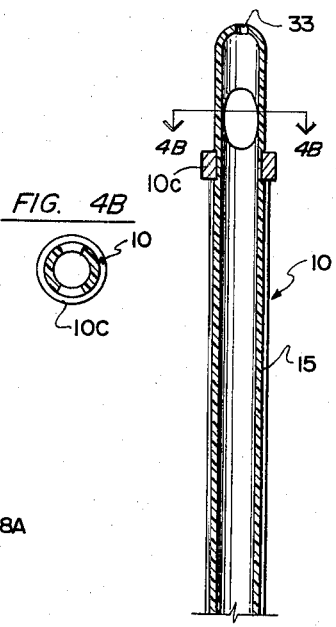
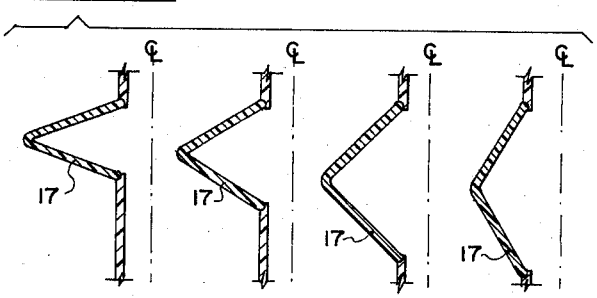
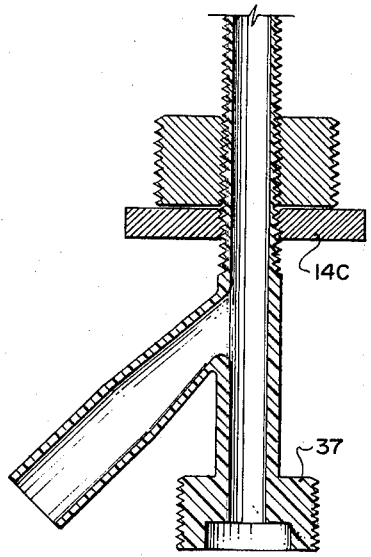

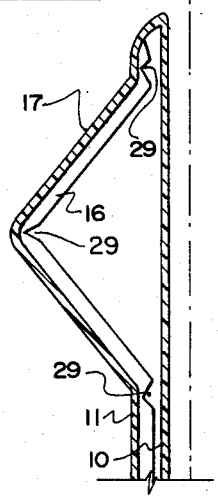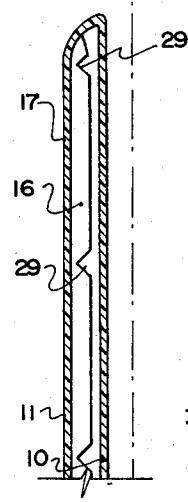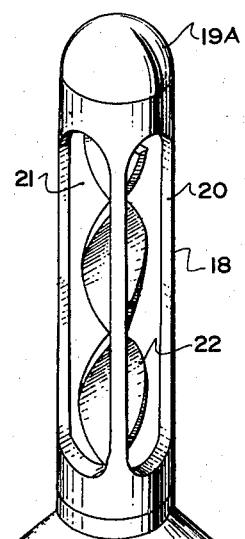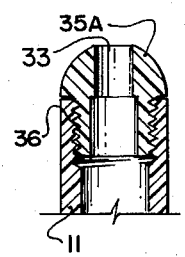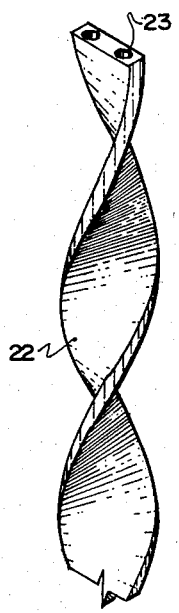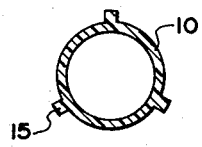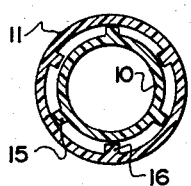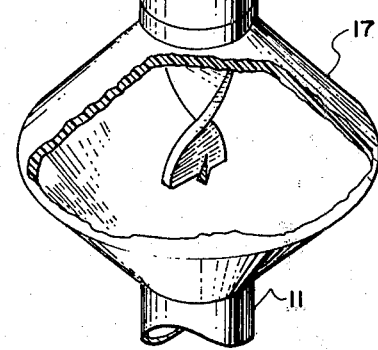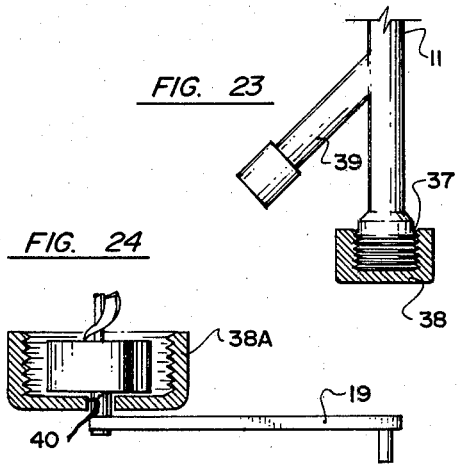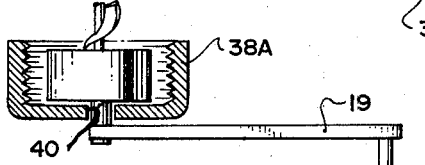

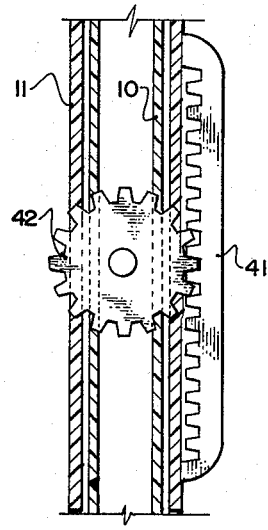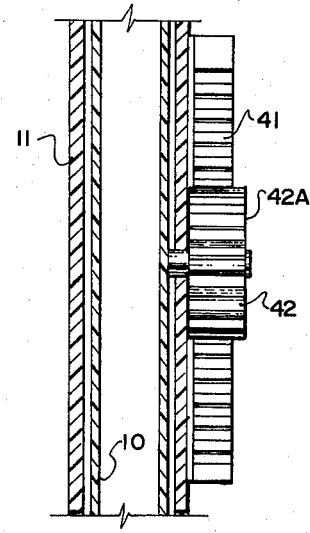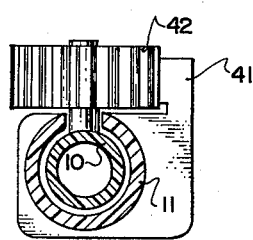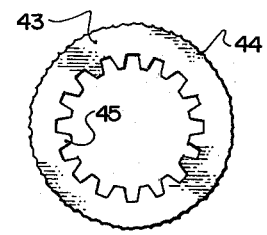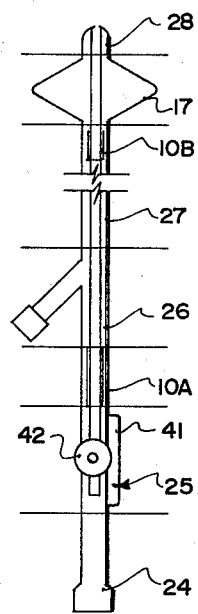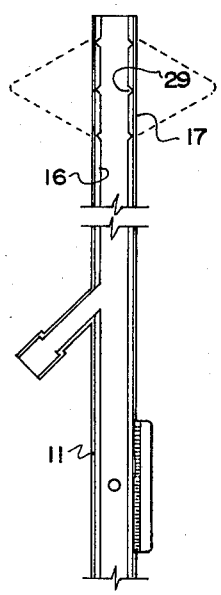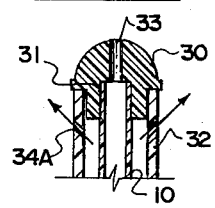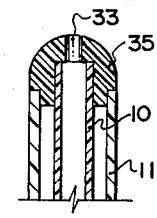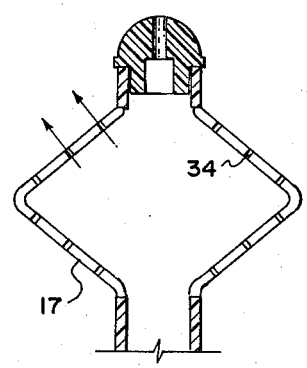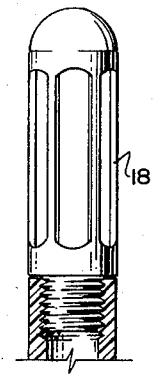

SELF-INFLATING AND SELF-CLEANING CATHETER ASSEMBLY

BACKGROUND OF THE INVENTION

This invention relates to new and useful improvements in catheters and, as conceived, this new catheter is designed to replace the standard Foley catheter because of several advantages thereover.

This new catheter has advantages over the Foley catheter, particularly in post-operative use, because it is believed that it will perform better through reduced patient recovery time, increase in comfort, and in the reduction of the number of secondary infections; safely requiring less nursing or other personnel time and specific attention; less auxiliary parts for use, and may be provided at a price to make it more economical in the overall health care field.

SUMMARY OF THE INVENTION

The advantages of the proposed catheter over the Foley catheter are first in the inbuilt mechanical inflating and deflating provision to eliminate the necessity, time and cost of using a separate syringe and sterile water that is required for inflating and deflating the Foley catheter. Secondly, and if desired, in the provision of a patient or attendant operated spiral screw means to prevent the accumulation of blood clots from blocking the drainage passage. The spiral screw component in the drainage passage is intended to prevent blood clots and debris from blocking the drainage tube by causing this material to be conveyed out of the drainage passage through the action of the spiral screw conveyor when rotated, which could be at regular intervals or when and if required.

The rotating means is shown as a simple folding handle to avoid overall diameter bulk. The intent of the concept is to avoid bladder spasms by providing a means to ensure adequate, rapid drainage from the bladder by preventing blockage of the drainage passage.

The operation of the spiral screw conveyor may also provide another barrier, in addition to the closed drainage system, to secondary infection through the drainage passage, and offers the possibility of cross connection of passages within the catheter to allow irrigating liquids to be used to flush the spiral screw conveyor and passage at regular intervals should this be indicated as desirable.

The self-retaining and self-cleaning catheter is a new concept in urinary drainage catheters which represents an advance over the conventional Foley catheter.

Key advantages relate to improved drainage and irrigation flow capacities, manually controlled self-retention in and release from the bladder, facility for clearing clots, improved patient comfort, and reduced tendency or possibility for development of secondary infection.

In basic construction, the catheter comprises a pair of thin-walled elastomeric (or similar suitable material or composites thereof) tubes with reinforcing and guiding elements. The structure is such that one of the two tubes rests in the other, forming a flexible combination which provides a smooth outer surface in contact with the urethra, and a pair of interior lumens—the inner cylindrical lumen serving as the drainage channel and the second lumen, formed by the large cross-sectional space between the two tubes, providing the passage for introduction of irrigating fluid. At the distal end, a member holds the tubes in proper relation to each other, furnishes a safe termination in the event of contact with the bladder wall, and provides apertures for fluid passage and for the clot removal feature.

The terminating member also functions in co-operation with a specially formed, immediately adjacent section of the outer tube and with a manually operated actuator at the proximal, external end of the catheter. This enables a nurse or other responsible person to produce a graded circumferential expansion of the formed section of the outer tube. The result is the equivalent of the inflatable balloons built into some Foley catheters, but with the added advantage of being able to adjust the retention section size at will. In the event, for example, that an attempt is made to expand the retainer before it has passed completely into the bladder, the operator can readily reduce its size to enable deeper introduction of the catheter. Similarly, a simple manual operation suffices to reduce the retainer when the catheter is to be removed.

The proximal end of the catheter is a formed member which completes the assembly, provides the drainage and irrigation apertures, and includes the means of adjusting the retention section. It also provides the means of optionally (or full time) introducing the clot removal device into the center lumen: this device can be compared to an auger which is rotated by a suitable handle or other drive external to the formed endpiece of the catheter assembly, with the effect of drawing down the lumen clots or bits of debris which might otherwise tend to block the passage.

It is appropriate to observe that an important problem which can arise in prostate and bladder operations is the formation in the bladder of a jelly-like mass of clots. Clearing such a condition can presently require operating room procedures entailing suctioning or invasive entry into the bladder. An alternative version of the catheter clot-removal facility may have the potential for extracting material from such a mass in conjunction with a water jet adaptation to the assembly.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

FIG. 3 is a longitudinal cross sectional view of one possible configuration of the outer envelope together with the inflation and irrigation components, with one type of irrigation entry means shown.

FIG. 3A is a series of schematic sections showing approximate positions of the inflated contour at progressive positions.

FIG. 3B is a section along the line 3B—3B of FIG. 3.

FIG. 4 is a longitudinal cross sectional view of the drainage tube component.

FIG. 4B is a section along the line 4B—4B of FIG. 4.

FIG. 5 is a schematic side elevation of the rotating screw conveyor component assembly.

FIG. 6 is a cross sectional view of the drainage tube component in FIG. 2.

FIG. 7 is a cross sectional view of the outer envelope of FIGS. 2 and 3.

FIG. 8 is a cross sectional view of the in-dwelling part of the drainage tube component within the outer envelope.

FIG. 9 is a schematic side view of the assembly inflated.

FIG. 9A is a schematic side view of the assembly non-inflated.

FIG. 10 is a schematic side view of a clot entry head construction.

FIG. 11 is a fragmentary view of one embodiment of the screw conveyor.

FIG. 12 is a schematic side elevation showing one method of inflating the catheter inflation section.

FIG. 13 is a view at right angles to FIG. 12.

FIG. 14 is a schematic top plan view of FIG. 12.

FIG. 15 shows a plan view of one method of actuating the inflator.

FIG. 16 is a schematic side elevation of the assembled catheter reduced in scale and showing one method of producing same in modular component parts.

FIG. 17 is a schematic fragmentary partially sectioned view of the lower end of outer envelope portion.

FIG. 18 is a fragmentary cross sectional view showing one type of irrigation tip.

FIG. 19 is a view similar to FIG. 18, but showing another method of irrigation.

FIG. 20 is a view similar to FIG. 18, but showing a further irrigation tip.

FIG. 21 is a fragmentary cross sectional side elevation of yet another embodiment of FIG. 18.

FIG. 22 is a view similar to FIG. 21, but showing a further irrigation tip.

FIG. 23 is a fragmentary cross sectional partially schematic view of the lower end of the drain tube showing a closure cap therefor.

FIG. 24 is a view similar to FIG. 23, but showing a closure cap with provision for the auger handle assembly.

In the drawings like characters of reference indicate corresponding parts in the different figures.

DETAILED DESCRIPTION

Figure 1:
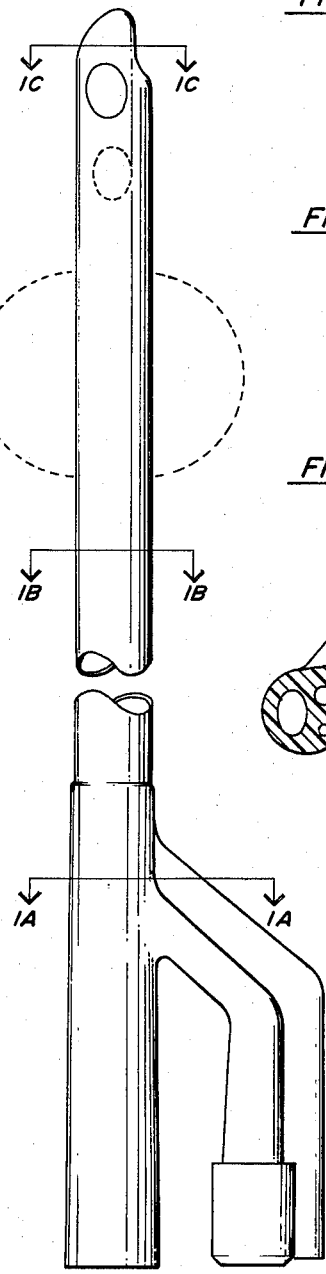
FIG. 1 is a side elevation of a conventional Foley catheter.
Figure 1C:
FIG. 1C is a cross section along the line 1C—1C of FIG. 1.
Figure 1B:
FIG. 1B is a cross section along the line 1B—1B of FIG. 1.
Figure 1A:
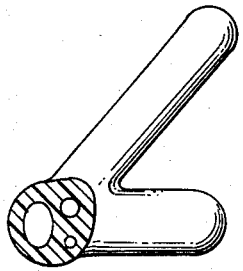
FIG. 1A is a cross section along the line 1A—1A of FIG. 1.

Proceeding therefore to describe the invention in detail, the catheter comprises three main parts which are intended to be factory assembled and provided in a sterile package to the using medical authorities. These parts are the inner part or drainage tube component 10, having a bore or lumen therethrough, the outer part or envelope 11 and the screw conveyor component 12 which may or may not be inserted depending upon circumstances.

These three main parts may be injection molded and be so manufactured that assembly is limited to fitting each part, in turn, inside the other, and securing the whole assembly together by two main threaded couplings 13 and 14 respectively and with the distal ends of the parts 10 and 11 being a force fit to hold the two parts firmly together at this point. Member 14C locks the assembly at a selected position.

The Foley catheter, shown in FIG. 1, is normally manufactured of latex rubber with a variety of coatings for low surface friction. Foley catheters have also been manufactured of silastic materials. Silicone rubber formulations, among other elastomers (or any other suitable flexible material) would be suitable for this new catheter.

The first requirement of any catheter is sufficient flexibility to accommodate to the curvi-linear contours of use, combined with sufficient rigidity to permit manipulation. In the present invention, the drainage tube component 10 and the outer envelope 11 are preferably thin walled units with two or more equally spaced longitudinally extending stiffening ribs 15 and 16 respectively around the outer and inner surfaces respectively of these components so that when inserted one within the other a floating fit is achieved, with the ribs 15 of the drainage tube component 10 alternating with the ribs 16 of the outer part 11. This defines a space or lumen between the two components which will be either filled with an irrigating liquid or air, so that, when in use, a cushioning effect will be obtained allowing, perhaps, for the use of slightly more rigid materials as some flexibility will be provided within this cushion.

This cushioning effect has also been provided in this design to absorb movement of the spiral screw conveyor 12 within the drainage tube 10 and to prevent, as much as possible, the transmission of any sense of rotation to the outer irrigation envelope 11 in contact with the inner wall of the urethra.

The operation of this catheter in a diameter comparable to the Foley catheter is dependent upon the formulation of a suitable elastomeric formulation or the equivalent capable of being injection molded or equivalent, extruded or otherwise forms, economically in the thin walled section and ribbing described. An alternative material could be a flexible vinyl as indicated by certain Russian studies. These, however, were carried out prior to recent work on gas emanations from vinyls which might make acceptance of such polymers difficult. Silastic and other suitable materials have been subjected to considerable test and evaluation.

The design of the new catheter is based on the provision of thin wall sections with interleaved ribbing between the outer irrigation envelope and the inner drainage passage channel to allow for an adequate drainage channel diameter suitable to drain the bladder and to make practical the use of a ribbon spiral conveyor 12.

FIG. 1 is a representation of a conventional Foley catheter, to which the design shown in the remaining drawings can be compared. All drawings are essentially schematic for visual comprison, and are enlarged for clarity.

Figure 2:
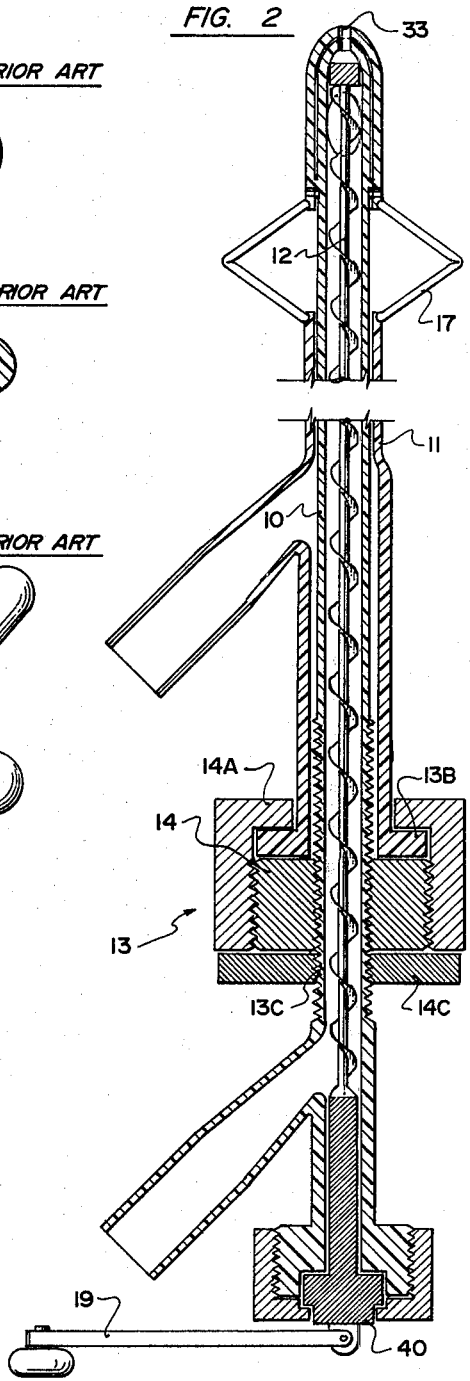
FIG. 2 is a longitudinal partially schematic, cross sectional view of an assembly of the improved catheter.

FIG. 2 is an assembly drawing of the three main components showing the essence of the design. An inbuilt mechanical inflating device 17 is also shown schematically. Essentially it comprises a series of longitudinal thin and thick sections or striations molded into the inflatable neck with appropriate bending creases to cause the section to take the contour and stretch to the dimensions shown on this drawing.

The threaded advancing nut assembly 13 includes an annular flange 13B formed on the lower end of the outer tube or envelope 11 with a screw threaded portion 13C being formed along the length of the drainage tube 10 within this area. An internally screw threaded nut 14 with an apertured upper portion 14A, screw threadably engages this screw threaded portion and the annular shoulder 13B so that rotation of the nut 14 upon the threaded portion 13C to move it in a downward direction with reference to FIG. 2, will draw the outer envelope downwardly relative to the drainage tube thus causing the inflatable or expandable portion 17 to expand as shown schematically in the drawings. Conversely, rotation of the nut 14 in the opposite direction will permit this portion 17 to collapse to the existing position due to the inherent resiliency of the material forming the device. However, if difficulty is experienced, then a relatively stiff rod or wire can be inserted through the drainage tube to the upper end thereof so that it engages the upper closed end of the outer envelope thereby permitting this envelope to be extended slightly thus collapsing the inflatable portion 17. Under certain circumstances, this "fail safe" method may be used but it is considered that such a condition would be rare. A lock nut 14C also engages the screw threaded portion 13C and may be tightened upwardly against the nut 14 when in the desired position to prevent inadvertent rotation thereof.

FIG. 3 shows the outer envelope. The inflation and irrigation component 11 has stiffening ribs 16 on the inner surface for the length of the catheter to be in contact with the urethra.

FIG. 4 illustrates the drainage tube component 10 per se, which has stiffening ribs 15 on the outer surface of the tubing so that when this component is inserted into the outer envelope 11, the stiffening ribs are interleaved, as it were, and as the ribs are not the full height of the space between the two tubing elements there is a provision for the cushion as previously mentioned (see FIG. 8). The drainage tube component 10 is a force fit into the outer element 11 at the insertion end of the catheter to prevent leakage from one channel to the other (the gland 10A is shown schematically in FIG. 16 and this detachably holds one within the other). At the other end of the catheter the two components are locked together by means of a second packing gland 10B at the inflation control assembly arrangement 17 or by means of a joining ring 10C around the inner tube 10 and secured to tube 10 and envelope 11 adjacent the distal end of the device.

FIG. 5 is an illustration of the rotating screw conveyor component 12 and shows the contour of this member which fits inside the drainage tube component 10 being locked at the bottom by a further packing gland 18A allowing the spiral screw to be rotated within the drainage tube 10 by the rotation of a turning handle 19 shown in the turning position on the assembly drawing FIG. 2 and in the folded down or stored position in FIG. 5. This spiral screw conveyor 12 may require slitting at the perimeter of the flighting to allow for accommodation to the curvature of the catheter when used in male patients. It is preferably made from plastic and comprises the screw or flighting 12A formed around the flexible shaft 12B.

FIG. 10 shows a clot entry head 18 that could be either added during manufacture to a catheter that was for this specific purpose including both the self-inflating and the clot entry head or the clot entry head could be an additional feature that simply attached to or could be screwed on to an ordinary catheter at the junction between the inflation section and the clot entry head section as shown in FIG. 10.

This clot entry head 18 includes the rounded tip 19A and the substantially cylindrical body portion 20 which is preferably provided with a plurality of longitudinally extending relatively wide apertures 21 as illustrated in FIG. 10 which communicate with the interior of the drainage tube 10.

Clots can be of the consistency of a jelly and these cannot be moved by an ordinary catheter. The head 18 is the largest cover possible for the auger extension 22 simply to protect it from hitting the top of the bladder or getting twisted into the side of the bladder but with wide open ports 21 so that the jelly would have to press around the side of it. It will be understood that this portion 22 is an extension of the auger assembly 12. If in addition to this, the extrusion screw shown in FIG. 11 is provided with holes or channels 23, it is possible that water or other fluids under pressure can be introduced into the self-cleaning part of the catheter as illustrated in FIG. 10 and with a sufficiently high pressure through exit holes at the top of the auger section, a high pressure spray would break down the jelly. If the auger is operated at a relatively high speed, there would be a very high volume transport of liquid or semisolid substances out of the bladder.

Although the inflation component 17 is shown spaced from the inner end of the catheter, it is believed desirable to position this as near to the inner end as possible in order to prevent the tip from irritating the bladder.

It will therefore be seen that a design is described and illustrated having advantages over the Foley catheter in the self-inflating and self-cleaning provisions.

As can be seen, the construction essentially calls for a very thin walled tubing with ribs, this being the case in both the inner and the outer parts 10 and 11 of the catheter. The input liquids to the bladder through the catheter flow within the space or lumen between the inner and the outer parts 10 and 11 of the catheter. This is for two reasons: one, it provides a large area cross section to allow for a massive introduction of fluids and it also allows for the outer and the inner parts to slip, one on the other, so that in connection with the self-inflating or expanding feature 17, of the catheter, the friction between the two parts is reduced which is, of course, important to their proper functioning. When liquids are being introduced into the bladder or passing through the catheter it would be as if the two parts had the friction resistance of elastomer to water.

Dealing next with FIGS. 16 through 24, these show schematic variations. FIG. 16 shows schematically how the catheter can be built up in separate sections. These are divided by transverse guide lines and as an example, the first portion 24 shows the output on the inner channel connection followed by the next section which is the inflating means generally designated 25. A packing gland 10A is next and then the irrigation input and the external to body irrigation connection, said section being identified by reference character 26. Reference character 27 shows the length of the catheter in the urethra followed by the inflation means or expansion means 17 and terminating in the tip assembly 28. These various sections provide not only for ease in manufacture but also for a certain flexibility in assembly so that the catheter may be used under various conditions. The concentrations between the sections may be either permanent as by adhesive or chemical means or temporary as, for example, by screw threading or other methods of detachable attachment. FIG. 16 is shown purely as an example of one way of forming the catheter in the various sections.

FIG. 17 shows the V-shaped grooves or notches 29 formed in the splines 16 in the area of the expanding portions 17 of the outer envelope 10, and also a portion of the preferred inflating means hereinafter to be described. These notches facilitate the outward positioning of the expanding portions 17 of the outer envelope.

The tip 19A may either take the form as shown in FIG. 10, or may be apertured as in FIG. 18 and indicated by reference character 30. This is provided with a shouldered lower portion 31 which engages within the upper cylindrical end 32 of the outer envelope and may be adhesively secured thereto. The central aperture 33 permits irrigation from the tip and communicating between the outside of the outer envelope 11, and the interior of the drainage tube 10. Alternatively, further irrigation, in the form of a spray, may be provided through apertures or drillings 34, formed in the walls of the outer envelope in the area 17 of the expansion portion, or through apertures or drillings 34A in the wall adjacent tip 30 (see FIG. 18). These apertures 34 and 34A constitute communication between the exterior of the outer envelope 11 and the interior thereof in the space or lumen between the inner surface of the outer envelope 11 and the outer surface of the drainage tube 10.

In FIG. 20, the tip specifically designated 35 is adapted to engage between the outer envelope and the drainage tube 11, once again being adhesively secured or secured by some similar means, with a central aperture or drilling 33 being provided therein.

In FIG. 21, the tip 35A is screw threadably enagaged within the end of the envelope 11, said screw threading connection being shown by reference character 36.

FIG. 22 shows a method of screw threadably securing the tip assembly 18 illustrated in FIG. 10. Alternatively, this assembly may be used for the dispersal of water or other suitable fluid for dissolving or dispersing bladder clots, or to introduce medication, or simply to irrigate the bladder. In both cases, other suitable fastening means can be used instead of the screw threading connection shown.

As shown in FIG. 23, at the lower end of the outer envelope 11, a screw threaded portion 37 may be formed on the end to receive a screw threaded cap 38 which closes this portion if the auger assembly 12 is not being used. This prevents leakage past the outer tube connection 39. If the auger assembly 12 is being used, as shown in FIG. 24, a similar cap 38A may be provided centrally apertured as at 40 to receive the stem of the handle assembly 19.

FIGS. 12 through 15 show a preferred arrangement of expanding and contracting the expansion portion 17 of the outer envelope. It includes a rack assembly 41 secured to the lower end of the outer envelope 11 with a gear 42 engageable therewith and secured to the inner drainage tube 10. The outer portion 42A of the gear extends beyond the plane of the rack so that an actuator 43 may be detachably engaged over the gear to rotate same. This actuator is a small cylinder preferably having a knurled outer surface 44 and a notched central aperture 45 with the notches corresponding to the gear teeth of the gear 42 so that it can be slipped over the exposed end 42A and engaged with the gear.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

What I claim as my invention is:

1. A catheter assembly for use as a urinary drainage device through the urethra; comprising in combination a flexible, longitudinally extending outer envelope, an inner drainage tube slidably engaging within said envelope, and means to detachably retain said catheter in position within the urethra, said means including an expanding portion formed along the length of said outer envelope adjacent the distal end thereof and extending uninterruptedly around the periphery thereof, mechanical means adjacent the proximal end of said outer envelope operatively connected to said expanding portion, to expand and retract said expanding portion, said expanding portion including means to facilitate the expansion of said expanding portion, said last mentioned means including a plurality of transversely notched splines formed on the inner wall of said expanding portion, means to detachably retain said inner drainage tube in position within said outer envelope, means to position said inner drainage tube within said outer envelope to define an annular longitudinally extending lumen between said drainage tube and said outer envelope, means communicating between the outside of said outer envelope and the interior of said drainage tube adjacent the distal ends thereof to convey fluids from outside of said outer envelope to the interior of said drainage tube and further means communicating between said lumen and the exterior of said outer envelope.

2. The assembly according to claim 1 in which said means to position said inner drainage tube centrally within said outer envelope includes a plurality of longitudinally extending ribs formed on and extending inwardly from the inner wall of said outer envelope, said ribs being in spaced relationship around said wall, and a plurality of longitudinally extending ribs formed on and extending outwardly from the outer wall of said drainage tube, said ribs interleaving with one another when said inner drainage tube is inserted within said outer envelope.

3. The assembly according to claim 2 in which the diameter defined by the inner ends of said ribs of said outer envelope is greater than the diameter of the outer wall of said drainage tube, the diameter defined by the outer ends of the ribs of said inner drainage tube having a diameter less than the inner diameter of said outer envelope.

4. The assembly according to claim 1 in which said mechanical means includes means to limit the movement of said inner drainage tube inwardly relative to said outer envelope and means to move the portion of said outer envelope between said expanding portion and proximal end of said envelope, towards said distal end of said envelope thereby forcing said expanding portion outwardly and vice-versa.

5. The assembly according to claim 2 in which said mechanical means includes means to limit the movement of said inner drainage tube inwardly relative to said outer envelope and means to move the portion of said outer envelope between said expanding portion and proximal end of said envelope, towards said distal end of said envelope thereby forcing said expanding portion outwardly and vice-versa.

6. The assembly according to claim 3 in which said mechanical means includes means to limit the movement of said inner drainage tube inwardly relative to said outer envelope and means to move the portion of said outer envelope between said expanding portion and proximal end of said envelope, towards said distal end of said envelope thereby forcing said expanding portion outwardly and vice-versa.

7. The assembly according to claim 4 in which said means to move the portion of said outer envelope comprises a shoulder formed on the proximal end of said outer envelope, a screw threaded portion on said drainage tube at said shoulder, and a nut screw threadably engaging said screw threaded portion of said drainage tube and frictionally engaging said shoulder whereby rotation of said nut moves said outer envelope relative to said drainage tube.

8. The assembly according to claim 5 in which said means to move the portion of said outer envelope comprises a shoulder formed on the proximal end of said outer envelope, a screw threaded portion on said drainage tube at said shoulder, and a nut screw threadably engaging said screw threaded portion of said drainage tube and frictionally engaging said shoulder whereby rotation of said nut moves said outer envelope relative to said drainage tube.

9. The assembly according to claim 6 in which said means to move the portion of said outer envelope comprises a shoulder formed on the proximal end of said outer envelope, a screw threaded portion on said drainage tube at said shoulder, and a nut screw threadably engaging said screw threaded portion of said drainage tube and frictionally engaging said shoulder whereby rotation of said nut moves said outer envelope relative to said drainage tube.

10. The assembly according to claim 4 in which said means to move the portion of said outer envelope comprises a rack portion formed on the proximal end of said drainage tube and a gear secured to said drainage tube and engageable with said rack, and means to selectively rotate said gear thereby moving outer envelope relative to said drainage tube.

11. The assembly according to claim 5 in which said means to move the portion of said outer envelope comprises a rack portion formed on the proximal end of said drainage tube and a gear secured to said drainage tube and engageable with said rack, and means to selectively rotate said gear thereby moving outer envelope relative to said drainage tube.

12. The assembly according to claim 6 in which said means to move the portion of said outer envelope comprises a rack portion formed on the proximal end of said drainage tube and a gear secured to said drainage tube and engageable with said rack, and means to selectively rotate said gear thereby moving outer envelope relative to said drainage tube.

13. The assembly according to claims 1, 2 or 3 which includes a detachable, flexible, longitudinally extending auger assembly engageable through the lumen of said drainage tube to adjacent the distal end thereof and means adjacent the proximal end of said drainage tube to selectively rotate said auger assembly.

14. The assembly according to claims 4, 5 or 6 which includes a detachable, flexible, longitudinally extending auger assembly engageable through the lumen of said drainage tube to adjacent the distal end thereof and means adjacent the proximal end of said drainage tube to selectively rotate said auger assembly.

15. The assembly according to claims 7, 8 or 9 which includes a detachable, flexible, longitudinally extending auger assembly engageable through the lumen of said drainage tube to adjacent the distal end thereof and means adjacent the proximal end of said drainage tube to selectively rotate said auger assembly.

16. The assembly according to claims 10, 11 or 12 which includes a detachable, flexible, longitudinally extending auger assembly engageable through the lumen of said drainage tube to adjacent the distal end thereof and means adjacent the proximal end of said drainage tube to selectively rotate said auger assembly.

17. A catheter assembly for use as a urinary drainage device through the urethra; comprising in combination a flexible, longitudinally extending outer envelope, an inner, longitudinally, centrally apertured, drainage tube engaged concentrically within said envelope, means to retain said inner drainage tube in position within said outer envelope, means to detachably retain said catheter in position in the urethra, means to position said inner drainage tube within said outer envelope to define an annular longitudinally extending lumen between said drainage tube and said outer envelope, and means communicating between the outside of said outer envelope and the interior of said drainage tube adjacent the distal ends thereof to convey fluids from the outside of said outer envelope and the interior of said drainage tube adjacent the distal ends thereof to convey fluids from the outside of said outer envelope to the interior of said drainage tube and further means communicating between said lumen and the exterior of said outer envelope, said means to position said inner drainage tube centrally within said outer envelope including a plurality of longitudinally extending ribs formed on and extending inwardly from the inner wall of said outer envelope, said ribs being in spaced relationship around said wall, and a plurality of longitudinally extending ribs formed on and extending outwardly from the outer wall of said drainage tube, said ribs interleaving with one another when said inner drainage tube is inserted within said outer envelope.

18. The assembly according to claim 17 in which the diameter defined by the inner ends of said ribs of said outer envelope is greater than the diameter of the outer wall of said drainage tube, the diameter defined by the outer ends of the ribs of said inner drainage tube having a diameter less than the inner diameter of said outer envelope.

* * * * *